(12) United States Patent
Edgell et al.

(10) Patent No.: US 10,556,119 B2
(45) Date of Patent: *Feb. 11, 2020

(54) COLOR CODED HEADER BORE IDENTIFICATION

(71) Applicant: Cardiac Pacemakers, Inc., St. Paul, MN (US)

(72) Inventors: John M. Edgell, Plymouth, MN (US); Keith R. Maile, New Brighton, MN (US); William J. Linder, Golden Valley, MN (US); Arthur J. Foster, Blaine, MN (US); Bryan J. Swackhamer, Shoreview, MN (US); Michael J. Kane, Roseville, MN (US); John Reardon, Tipperary (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 155 days.

This patent is subject to a terminal disclaimer.

(21) Appl. No.: 15/668,949

(22) Filed: Aug. 4, 2017

(65) Prior Publication Data

US 2017/0354829 A1   Dec. 14, 2017

Related U.S. Application Data

(63) Continuation of application No. 14/498,111, filed on Sep. 26, 2014, now Pat. No. 9,724,527.

(Continued)

(51) Int. Cl.
*A61N 1/375* (2006.01)
*A61N 1/39* (2006.01)
*B41F 17/00* (2006.01)

(52) U.S. Cl.
CPC ......... *A61N 1/3968* (2013.01); *A61N 1/3752* (2013.01); *B41F 17/00* (2013.01); *A61N 1/3962* (2013.01)

(58) Field of Classification Search
None
See application file for complete search history.

(56) References Cited

U.S. PATENT DOCUMENTS 5,383,914 A   1/1995   O'Phelan
5,626,626 A   5/1997   Carson
(Continued)

OTHER PUBLICATIONS

"U.S. Appl. No. 14/498,111, Advisory Action dated Jun. 30, 2016", 5 pgs.

(Continued)

*Primary Examiner* — Kennedy Schaetzle
(74) *Attorney, Agent, or Firm* — Schwegman Lundberg & Woessner, P.A.

(57) ABSTRACT

An implantable pulse generator includes a device housing containing pulse generator circuitry and a header connected to the device housing. The header includes a core assembly defining first and second lead bore cavities sized for receiving terminal pins of leads, first and second labels, and an outer layer. The first label is printed onto a surface of the core assembly proximate the first lead bore cavity and includes a first color. The second label is printed onto the surface of the core assembly proximate the second lead bore cavity and includes a second color different from the first color. The outer layer is overmolded over the core assembly so as to encapsulate the first and second labels and to allow access to the first and second lead bore cavities.

20 Claims, 6 Drawing Sheets

Related U.S. Application Data

(60) Provisional application No. 61/883,478, filed on Sep. 27, 2013.

(56) References Cited

U.S. PATENT DOCUMENTS

| | | | |
|---|---|---|---|
| 5,679,026 A | 10/1997 | Fain et al. |
| 6,672,895 B2 | 1/2004 | Scheiner |
| 6,847,845 B2 | 1/2005 | Belden |
| 6,968,235 B2 | 11/2005 | Belden et al. |
| 6,975,906 B2 | 12/2005 | Rusin et al. |
| 7,155,283 B2 | 12/2006 | Ries et al. |
| 7,195,523 B2 | 3/2007 | Naviaux |
| 7,239,916 B2 | 7/2007 | Thompson et al. |
| 7,274,963 B2 | 9/2007 | Spadgenske |
| 7,903,043 B2 | 3/2011 | Prashant et al. |
| 8,019,420 B2 | 9/2011 | Hine et al. |
| 8,029,482 B2 | 10/2011 | Maniar et al. |
| 8,096,838 B2 | 1/2012 | Dilmaghanian |
| 8,167,660 B2 | 5/2012 | Dilmaghanian et al. |
| 8,200,335 B2 | 6/2012 | Donofrio et al. |
| 8,214,046 B2 | 7/2012 | Alexander et al. |
| 8,248,232 B2 | 8/2012 | Stevenson et al. |
| 8,290,593 B2 | 10/2012 | Libbey et al. |
| 8,366,475 B2 | 2/2013 | Smith et al. |
| 8,543,209 B2 | 9/2013 | Tyers et al. |
| 8,731,671 B2 | 5/2014 | Rodby et al. |
| 9,724,527 B2 | 8/2017 | Edgell et al. |
| 2002/0107546 A1 | 8/2002 | Ostroff et al. |
| 2003/0018364 A1 | 1/2003 | Belden et al. |
| 2003/0040780 A1 | 2/2003 | Haeg et al. |
| 2003/0050680 A1 | 3/2003 | Gibson et al. |
| 2004/0019360 A1 | 1/2004 | Farnsworth et al. |
| 2004/0230269 A1 | 11/2004 | Huff et al. |
| 2005/0075707 A1 | 4/2005 | Meadows et al. |
| 2006/0030204 A1 | 2/2006 | Jones et al. |
| 2006/0206151 A1 | 9/2006 | Lu |
| 2006/0259092 A1 | 11/2006 | Spadgenske et al. |
| 2006/0282144 A1 | 12/2006 | Knapp et al. |
| 2007/0123947 A1 | 5/2007 | Wenger et al. |
| 2007/0160814 A1 | 7/2007 | Mercolino |
| 2008/0009718 A1 | 1/2008 | Zohman |
| 2008/0037131 A1 | 2/2008 | Steenblik et al. |
| 2008/0046059 A1 | 2/2008 | Zarembo et al. |
| 2009/0018601 A1 | 1/2009 | Deininger et al. |
| 2009/0234427 A1 | 9/2009 | Chinn et al. |
| 2010/0114210 A1 | 5/2010 | Donofrio et al. |
| 2011/0190833 A1 | 8/2011 | Ries et al. |
| 2011/0270065 A1 | 11/2011 | Ternes et al. |
| 2011/0271856 A1 | 11/2011 | Fisher et al. |
| 2012/0203302 A1 | 8/2012 | Moffitt et al. |
| 2013/0150916 A1 | 6/2013 | Kane et al. |
| 2013/0267837 A1 | 10/2013 | Schulte et al. |
| 2014/0257444 A1 | 9/2014 | Cole et al. |
| 2015/0094791 A1 | 4/2015 | Edgell et al. |

OTHER PUBLICATIONS

"U.S. Appl. No. 14/498,111, Final Office Action dated Mar. 31, 2016", 20 pgs.

"U.S. Appl. No. 14/498,111, Non Final Office Action dated Aug. 31, 2016", 17 pgs.

"U.S. Appl. No. 14/498,111, Non Final Office Action dated Sep. 18, 2015", 13 pgs.

"U.S. Appl. No. 14/498,111, Notice of Allowance dated Mar. 30, 2017", 8 pgs.

"U.S. Appl. No. 14/498,111, Response filed May 31, 2016 to Final Office Action dated Mar. 31, 2016", 13 pgs.

"U.S. Appl. No. 14/498,111, Response filed Jun. 30, 2016 to Final Action dated Jun. 30, 2016", 16 pgs.

"U.S. Appl. No. 14/498,111, Response filed Nov. 30, 2016 to Non Final Office Action dated Aug. 31, 2016", 17 pgs.

"U.S. Appl. No. 14/498,111, Response filed Dec. 18, 2015 to Non Final Office Action dated Sep. 18, 2015", 15 pgs.

COLOR CODED HEADER BORE IDENTIFICATION

CLAIM OF PRIORITY

This application is a continuation of U.S. application Ser. No. 14/498,111, filed Sep. 26, 2014, which claims priority to Provisional Application No. 61/883,478, filed Sep. 27, 2013, each of which is herein incorporated by reference in its entirety.

TECHNICAL FIELD

The present invention relates to implantable medical devices. More specifically, the invention relates to headers for implantable medical devices.

BACKGROUND

Various physiological functions can be managed and/or monitored using medical devices. Many such medical devices are implantable in a human body, such as implantable cardioverter-defibrillators (ICDs) or pacemakers. Such devices typically include a housing enclosing the device and may or may not include one or more medical electrical leads that can transmit electrical signals to and/or from a sensor, electrode, or other electrical component at a distal end of the medical electrical lead. For example, such devices have been used in association with cardiac rhythm management, which can include cardiac pacing, cardiac defibrillation, and/or cardiac therapy, among other procedures.

In some such devices, an implantable medical device includes a housing with a header having one or more lead bore cavities for receiving and connecting to one or more medical electrical leads. In embodiments where the header has multiple lead bore cavities, each lead bore cavity can be designated for connection to a specific medical electrical lead. The implantable medical device can fail to function or function incorrectly if a medical electrical lead is inserted in an incorrect lead bore cavity of the header.

SUMMARY

Disclosed herein are various embodiments of implantable pulse generators.

In Example 1, an implantable pulse generator includes a device housing containing pulse generator circuitry and a header connected to the device housing. The header includes a core assembly defining first and second lead bore cavities sized for receiving terminal pins of leads, a first label printed onto a surface of the core assembly proximate the first lead bore cavity, a second label printed onto the surface of the core assembly proximate the second lead bore cavity, and an outer layer overmolded over the core assembly so as to encapsulate the first and second labels and to allow access to the first and second lead bore cavities. The first label includes a first color and the second label includes a second color different from the first color.

In Example 2, the implantable pulse generator according to Example 1, wherein the core assembly comprises an engineered thermoplastic polyurethane and the outer layer comprises an epoxy resin that bonds to the core assembly so as to isolate the first and second labels from an exterior of the header.

In Example 3, the implantable pulse generator according to any of Examples 1-2, and further including a lenticular lens positioned proximate the first label.

In Example 4, the implantable pulse generator according to any of Examples 1-3, wherein the header further includes a magnifying lens positioned proximate the first label so as to magnify the first label.

In Example 5, the implantable pulse generator according to any of Examples 1-4, wherein the outer layer is transparent.

In Example 6, the implantable pulse generator according to any of Examples 1-5, and further including a first lead having a first terminal pin and a third label comprising the first color and a second lead having a second terminal pin and a fourth label comprising the second color. The first terminal pin is positioned in the first lead bore cavity and the second terminal pin is positioned in the second lead bore cavity.

In Example 7, the implantable pulse generator according to any of Examples 1-6, wherein the first label includes radiopaque ink patterned to define a first indicia that is viewable via radiology imaging systems and the second label includes radiopaque ink patterned to define a second indicia that is viewable via radiology imaging systems and that is different from the first indicia.

In Example 8, the implantable pulse generator according to any of Examples 1-7, wherein the first label comprises ink patterned as a first indicia that is viewable in the visible light spectrum and the second label comprises ink patterned as a second indicia that is viewable in the visible light spectrum and that is different from the first indicia.

In Example 9, the implantable pulse generator according to any of Examples 1-8, wherein the first lead bore cavity is a defibrillation lead bore cavity configured for connecting to a defibrillation lead terminal pin, the second lead bore cavity is a pacing lead bore cavity configured for connecting to a pacing lead terminal pin, the core further defines a low-voltage lead bore cavity configured for connecting to a low-voltage lead terminal pin, the first label is a red-pigmented label positioned proximate the defibrillation lead bore cavity, the second label is a white-pigmented label positioned proximate the pacing lead bore cavity, and further including a green-pigmented label printed onto the surface of the core assembly proximate the low-voltage lead bore cavity.

In Example 10, the implantable pulse generator according to Example 9, wherein the red-pigmented label comprises a red-pigmented portion and a first white-pigmented portion and wherein the green-pigmented label comprises a green-pigmented portion and a second white pigmented portion.

In Example 11, the implantable pulse generator according to any of Examples 9-10, wherein the red-pigmented label includes no green-pigmented portion and wherein the green-pigmented label contains no red-pigmented portion.

In Example 12, the implantable pulse generator according to any of Examples 1-11, wherein the first label includes a first machine-readable indicia and where the second label includes a second machine-readable indicia different from the first machine-readable indicia.

In Example 13, a method of labeling a header of an implantable pulse generator includes printing a first label of a first color onto a surface of a core assembly proximate a first lead bore cavity, printing a second label of a second color different from the first color onto the surface proximate a second lead bore cavity, and overmolding an outer layer over the core assembly so as to encapsulate the first and second labels and to allow access to the first and second lead bore cavities.

In Example 14, the method according to Example 13, wherein the first label comprises a first colored pigment not identified in any of 21 C.F.R. 73 (Listing of Color Additives Exempt From Certification), 21 C.F.R. 74 (Listing of Color Additives Subject to Certification), and (21 C.F.R. 82 Listing of Certified Provisionally Listed Colors and Specifications), and the second label comprises a second colored pigment not identified in any of 21 C.F.R. 73 (Listing of Color Additives Exempt From Certification), 21 C.F.R. 74 (Listing of Color Additives Subject to Certification), and (21 C.F.R. 82 Listing of Certified Provisionally Listed Colors and Specifications) and that is different from the first colored pigment.

In Example 15, the method according to any of Examples 13-14, and further including patterning a first set of indicia onto the first label and a second set of indicia different from the first set of indicia onto the second label.

In Example 16, an implantable pulse generator includes a device housing containing pulse generator circuitry and a header connected to the device housing. The header defines first and second lead bore cavities sized for receiving terminal pins of leads. A first label is positioned on a first portion of the header proximate the first lead bore cavity, wherein the first label comprises a first colored pigment not identified in any of 21 C.F.R. 73 (Listing of Color Additives Exempt From Certification), 21 C.F.R. 74 (Listing of Color Additives Subject to Certification), and (21 C.F.R. 82 Listing of Certified Provisionally Listed Colors and Specifications). A second label is positioned on a second portion of the header proximate the second lead bore cavity, wherein the second label comprises a second colored pigment not identified in any of 21 C.F.R. 73 (Listing of Color Additives Exempt From Certification), 21 C.F.R. 74 (Listing of Color Additives Subject to Certification), and (21 C.F.R. 82 Listing of Certified Provisionally Listed Colors and Specifications). An outer layer encapsulates the first and second labels and allows access to the first and second lead bore cavities.

In Example 17, the implantable pulse generator according to Example 16, wherein the first lead bore cavity is a defibrillation lead bore cavity configured for connecting to a defibrillation lead terminal pin, the second lead bore cavity is a pacing lead bore cavity configured for connecting to a pacing lead terminal pin, the header further defines a low-voltage lead bore cavity configured for connecting to a low-voltage lead terminal pin, the first label is a red-pigmented label positioned proximate the defibrillation lead bore cavity, the second label is a white-pigmented label positioned proximate the pacing lead bore cavity, and further comprising a green-pigmented label positioned on a third portion of the header proximate the low-voltage lead bore cavity.

In Example 18, the implantable pulse generator according to claim 17, wherein the red-pigmented label comprises a red-pigmented portion and a first white-pigmented portion and wherein the green-pigmented label comprises a green-pigmented portion and a second white pigmented portion.

In Example 19, the implantable pulse generator according to any of claims 17-18, wherein the red-pigmented label includes no green-pigmented portion and wherein the green-pigmented label contains no red-pigmented portion.

In Example 20, the implantable pulse generator according to any of claims 17-19, and further including a defibrillation lead, a pacing lead, and a low voltage lead. The defibrillation lead has a defibrillation lead terminal pin and a first lead label of a hue that is substantially the same as that of the red-pigmented label, wherein the defibrillation lead terminal pin is positioned in the defibrillation lead bore cavity. The pacing lead has a pacing lead terminal pin and a second lead label of a hue that is substantially the same as that of the white-pigmented label, wherein the pacing lead terminal pin is positioned in the pacing lead bore cavity. The low-voltage lead has a low-voltage lead terminal pin and a third lead label of a hue that is substantially the same as that of the green-pigmented label, wherein the low-voltage lead terminal pin is positioned in the low-voltage lead bore cavity.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
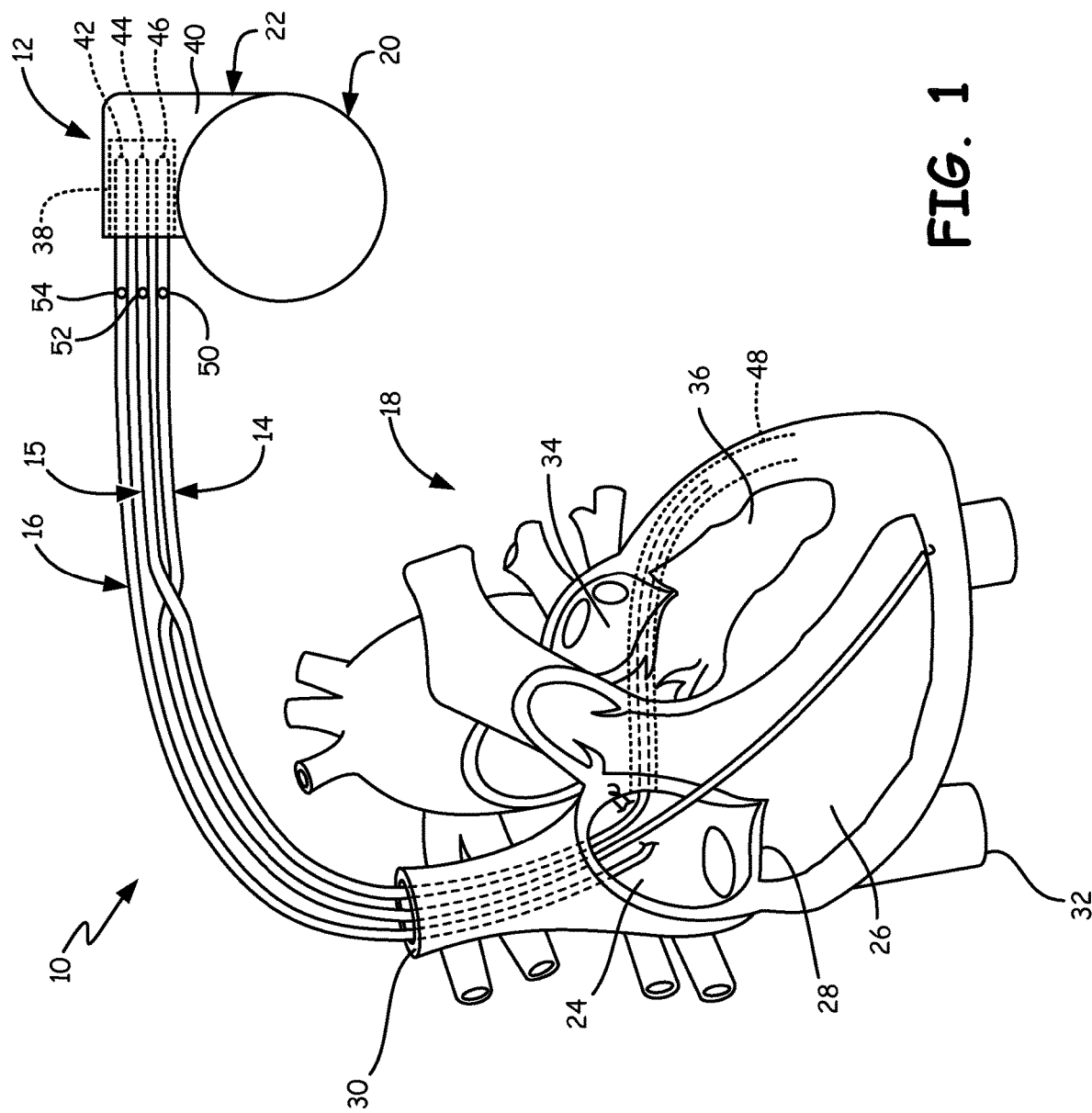
FIG. 1 is a schematic view of a cardiac rhythm management (CRM) system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to one embodiment. As shown in FIG. 1, the CRM system 10 includes a pulse generator 12 coupled to a plurality of leads 14, 15, and 16 deployed in a patient's heart 18. The pulse generator 12 includes a housing 20 and a header 22 mounted on the housing 20. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. As further shown, the heart 18 includes a left atrium 34, which receives oxygenated blood from the lungs, and a left ventricle 36, which pumps the oxygenated blood to the body.

The header 22 of the pulse generator 12 is an output terminal header with a core assembly 38 substantially encapsulated in a header body 40. The core assembly 38 defines lead bore cavities 42, 44, and 46 for receiving proximal ends of the leads 16, 15, and 14, respectively.

In the embodiment illustrated in FIG. 1, the leads 14, 15 and 16 extend from the pulse generator 12 through the superior vena cava 30 and into the right atrium 24. The leads 14, 15, and 16 are medical electrical leads that operate to convey electrical signals and stimuli between the heart 18 and the pulse generator 12. In the particular embodiment illustrated in FIG. 1, the CRM system 10 is a cardiac resynchronization therapy (CRT) system configured for bi-ventricular pacing. As shown, the lead 14 has a distal end secured within the right ventricle 26, the lead 15 extends into a coronary vein 48 for stimulating the left ventricle 36, and the lead 16 has its distal end secured within the right atrium 24. In various embodiments, the CRM system 10 is a CRT system with defibrillation/cardioversion capabilities (i.e., a CRT-D system). In such embodiments, the lead 14 can also be a defibrillation lead with single or dual high-voltage shocking coil electrodes disposed along its length. In alternative embodiments, the lead 15 can be omitted. In further alternative embodiments, additional leads (not shown) can be included as appropriate for a given application.

Lead labels 50, 52, and 54 are positioned on leads 14, 15, and 16, respectively. The lead labels 50, 52, and 54 can include one or more colors and/or one or more indicia providing an indication of one or more characteristics of the respective lead. Exemplary characteristics can include, without limitation, structural or functional lead features (e.g., defibrillation capabilities, multi-polar electrode configurations, and the like) or implantation locations (e.g., right ventricle, left ventricle, right atrium, etc.). Suitable indicia can include one or more letters, numbers, shapes, images, and/or machine-readable indicia such as bar codes, magnetic stripes or other machine-readable indicia. For example, in one embodiment the label 50 can be red-pigmented, the label 52 can be green-pigmented, and the label 54 can be white-pigmented.

The pulse generator 12 can be implanted subcutaneously within an implantation location or pocket in the patient's chest or abdomen. The pulse generator 12 can be any implantable medical device known in the art, or later developed, for delivering an electrical therapeutic stimulus to the patient. In various embodiments, the pulse generator 12 can be a neurostimulation device, a pacemaker, a CRT device, an implantable cardiac defibrillator, and/or can include both pacing, CRT and/or defibrillation capabilities (e.g., a CRT-D device).

In some embodiments the CRM system 10 can be configured to stimulate cardiac tissue and/or sense certain physiological attributes of the heart. However, in discussing embodiments of the present disclosure, reference is made primarily to stimulating body tissues. Those of ordinary skill in the art will recognize that some or all of the configurations can also be used to receive electrical signals from the body.

Figure 2:
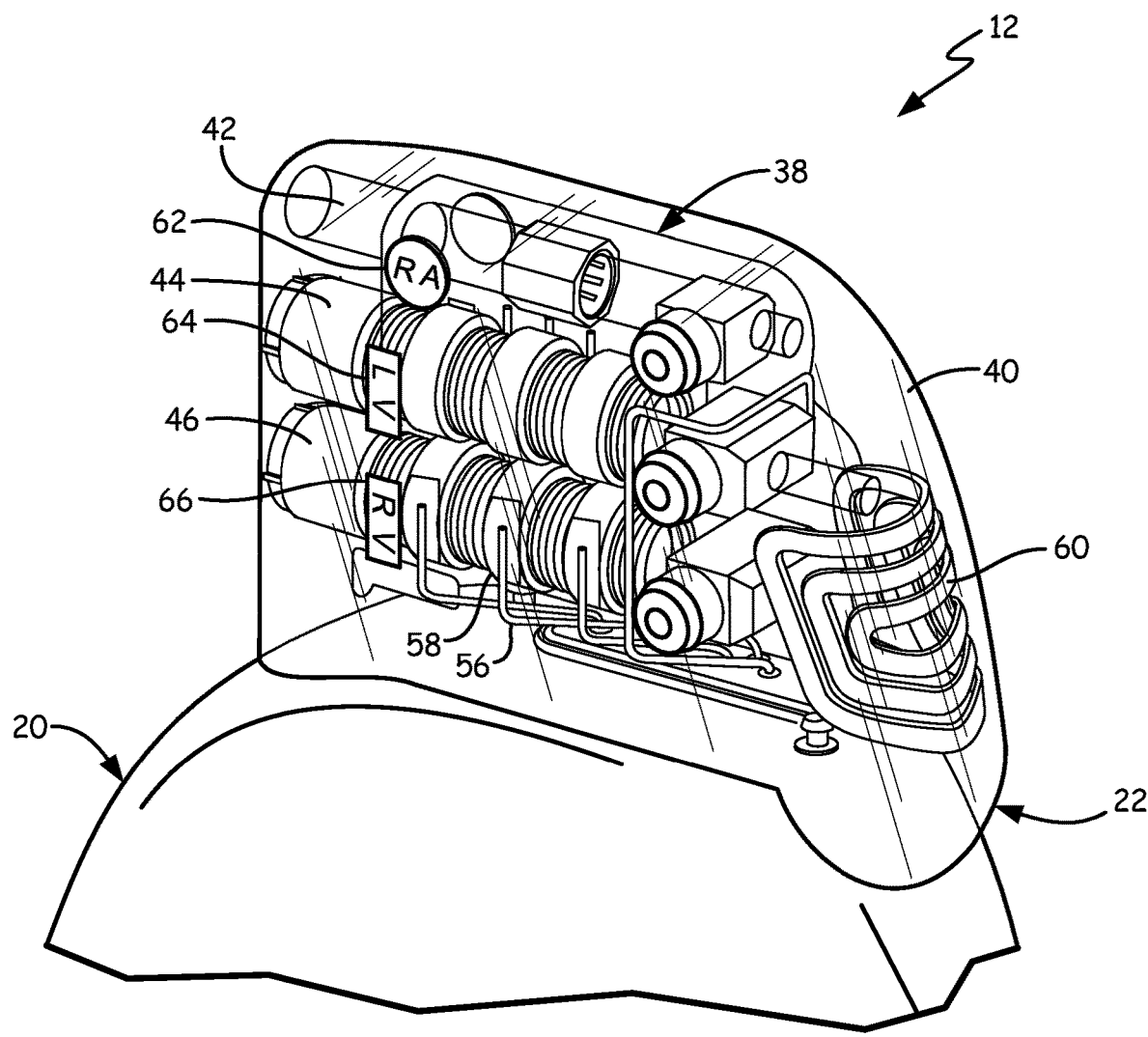
FIG. 2 is a perspective view of one embodiment of a pulse generator for use in the CRM system of FIG. 1.

FIG. 2 is a perspective view of a portion of the pulse generator 12 showing the header body 40 as transparent. In the illustrated embodiment, the core assembly 38 is encapsulated in the header 22, with the header body 40 overmolded over the core assembly 38. The lead bore cavities 42, 44, and 46 extend through portions of both the header body 40 and the core assembly 38, and are thus defined by both the header body 40 and the core assembly 38.

A plurality of electrical leads 56 connect pulse generator circuitry (not shown) within the housing 20 to electrical contacts 58 on the core assembly 38. Thus, the pulse generator 12 can transmit electrical signals to and from leads (such as the leads 14, 15, and 16, shown in FIG. 1) connected to the electrical contacts 58 in the header 22. The header 22 can also include an antenna 60 electrically connected to the pulse generator circuitry in the housing 20 for allowing remote communication with the pulse generator 12. The electrical leads 56, the electrical contacts 58, and the antenna 60 can all be overmolded and encapsulated by the header body 40.

In the illustrated embodiment, the core assembly 38 is a single core defining each of the lead bore cavities 42, 44, and 46. In alternative embodiments, the core assembly 38 can include multiple interconnected cores, each defining a different one of the lead bore cavities 42, 44, and 46. In further embodiments, the header 22 can include components and be configured differently, as suitable for a given application.

As shown in FIG. 2, the header 22 includes labels 62, 64, and 66 on the core assembly 38 encapsulated by the header body 40. In the illustrated embodiment, the label 62 is positioned on a portion of the header 22 proximate the lead bore cavity 42. The label 64 is positioned on a portion of the header 22 proximate the lead bore cavity 44. The label 66 is positioned on a portion of the header 22 proximate the lead bore cavity 46. The labels 62, 64, and 66 are encapsulated by the header body 40.

The labels 62, 64, 66 can include one or more colors and/or one or more indicia. Suitable indicia can include one or more letters, numbers, shapes, images, and/or machine-readable indicia such as bar codes, magnetic stripes or other machine-readable indicia. Such indicia can identify and/or provide information relating to the lead bore cavities 42, 44, and 46. For example, in the illustrated embodiment, the lead bore cavity 42 is configured to receive a pacing lead positioned within the right atrium. As such, the label 62 includes the indicia of "RA" to indicate right atrium. Similarly, the lead bore cavity 44 is configured to receive a left ventricular stimulation lead, and thus the label 64 includes the indicia "LV" to indicate left ventricle. In addition, the lead bore cavity 46 is configured to receive a lead positioned in the right ventricle, and as such, the label 66 includes the indicia "RV" to indicate right ventricle. Thus, including indicia on the labels 62, 64, and 66 can ensure visual indication to the physician that the correct leads 14, 15, and 16 (shown in FIG. 1) are inserted into the correct lead bore cavities 46, 44, and 42, respectively.

In the illustrated embodiment, the lead bore cavities 44 and 46 are both multi-polar, specifically, quad-polar lead bore cavities configured to operatively receive respective quad-polar leads. In one embodiment, the lead bore cavity 44 is configured to operatively receive a terminal connector conforming to the IS-4 standard for multi-polar low-voltage leads, while the lead bore cavity 46 is configured to operatively receive a terminal connector conforming to the DF4 standard for high-voltage multi-polar leads. Because of structural similarities between IS4 and DF4 standard lead terminal connectors, in some embodiments, the lead bore cavity 46 may also be capable of at least partially receiving and operatively coupling to an IS4 connector of a low-voltage lead. Including the indicia on the labels 64 and 66 can operate to provide additional visual indication as to the type of lead bore cavity into which the respective lead is being inserted.

The labels 62, 64, and 66 can include colors in addition to or instead of indicia. For example, the label 62 can be white-pigmented in addition to including the indicia of RA. The label 64 can be green-pigmented in addition to including the indicia of LV. The label 66 can be red-pigmented in addition to including the indicia of RV. Alternatively, the labels 62, 64, and 66 can be white, green, and red-pigmented (respectively) without including any indicia. In further alternative embodiments, the labels 62, 64, and 66 can include different colors and/or indicia as suitable for the application.

In some embodiments, the labels 62, 64, and 66 can include multiple colors. For example, the label 62 can be white with black indicia, the label 64 can be green with white indicia, and the label 66 can be red with white indicia. In some embodiments, labels can include at least some dedicated colors. For example, in one embodiment the label 64 can include a green pigmented portion and no red pigmented portion, and the label 66 can include a red pigmented portion and no green pigmented portion.

In embodiments where the labels 62, 64, and 66 include machine-readable indicia, the respective labels 62, 64, and 66 can each include unique machine-readable indicia that are different from each other, allowing a machine to distinguish between the labels 62, 64, and 66.

In embodiments where the labels 62, 64, and 66 are colored, the labels 62, 64, and 66 can have the same or similar color to that of the labels 54, 52, and 50 (shown in FIG. 1), respectively. In one embodiment, each of the labels 62, 64, and 66 can have the same color in the same hue as that on a respective one of the labels 54, 52, and 50. Color-coding the respective labels 62, 64 and 66 can act as a confirmation feature to help ensure that the correct leads 14, 15, and 16 (shown in FIG. 1) are inserted into the correct lead bore cavities 46, 44, and 42, respectively.

Figure 3:
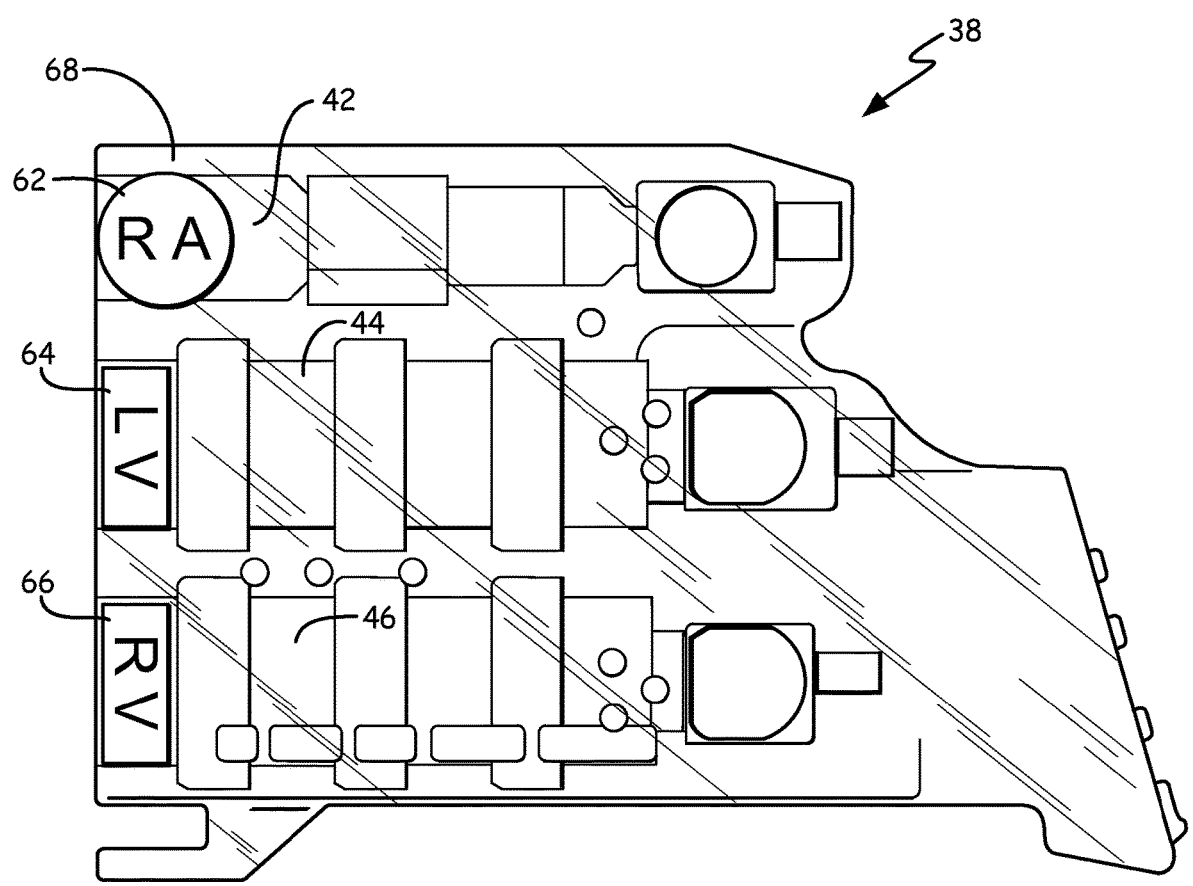
FIG. 3 is a side view of a core assembly for use in the pulse generator of FIG. 2.

FIG. 3 is a side view of the core assembly 38 according to an exemplary embodiment. In the illustrated embodiment, the labels 62, 64, and 66 are disposed on an outer surface 68 of the core assembly 38, proximate the respective lead bore cavities 42, 44, and 46. In one embodiment, the labels 62, 64, 66 are disposed on the outer surface 68 via a printing process. Printing the labels 62, 64, and 66 onto the core assembly 38 can simplify the manufacturing process as opposed to using separately printed labels and can allow the labels 62, 64, and 66 to be encapsulated when the header body 40 (shown in FIGS. 1 and 2) is molded over the core assembly 38. In alternative embodiments, the labels 62, 64, and 66 can be encapsulated via another layer instead of, or in addition to, the header body 40.

In embodiments where the labels 62, 64, and 66 are encapsulated, the labels 62, 64, and 66 can be substantially physically and fluidly isolated from the external environment so as to limit or prevent patient contact with ink on the labels 62, 64, and 66. Substantially or completely isolating the printed labels 62, 64, 66 from contact with the patient allows a wide range of potential pigments to be suitable for use in pigmenting the labels 62, 64, and 66. In one embodiment, the labels 62, 64, and/or 66 can use one or more pigments not identified in 21 C.F.R. 73 (Listing of Color Additives Exempt From Certification), 21 C.F.R. 74 (Listing of Color Additives Subject to Certification), and (21 C.F.R. 82 Listing of Certified Provisionally Listed Colors and Specifications). For example, the label 62 can include an ultraviolet curable white ink that includes titanium dioxide and the label 66 can include an ultraviolet curable red ink that includes quinacridone compound.

In some embodiments, the labels 62, 64, and 66 can include bright or high-contrast pigments that are viewable in the visible light spectrum. This can help visually distinguish the labels 62, 64, and 66 from one another. In one embodiment, the labels 62, 64, and 66 can be printed using fluorescent brightener. Use of fluorescent brightener can alter perception of an off-white portion of the labels 62, 64, and 66 to appear more white. Use of fluorescent brightener can also allow the labels 62, 64, and 66 to stand out when exposed to a black light. In another embodiment, the labels 62, 64, and 66 can be printed using an ink that stands out when exposed to a light source other than white light, such as ultraviolet light, infrared light, or a monochromatic light within the visible spectrum. In a further alternative embodiment, the labels 62, 64, and 66 can be printed using reflective ink.

In one embodiment, the core assembly 38 can comprise an engineered thermoplastic polyurethane material and the header body 40 can comprise an epoxy resin material that bonds to the core assembly 38 so as to substantially or wholly isolate the labels 62, 64, and 66 from the exterior of the header 22. In alternative embodiments, the core assembly 38 and/or the header body 40 can be formed of one or more other material suitable for sealing the labels 62, 64, and 66 from the exterior of the header 22.

Figure 4A:
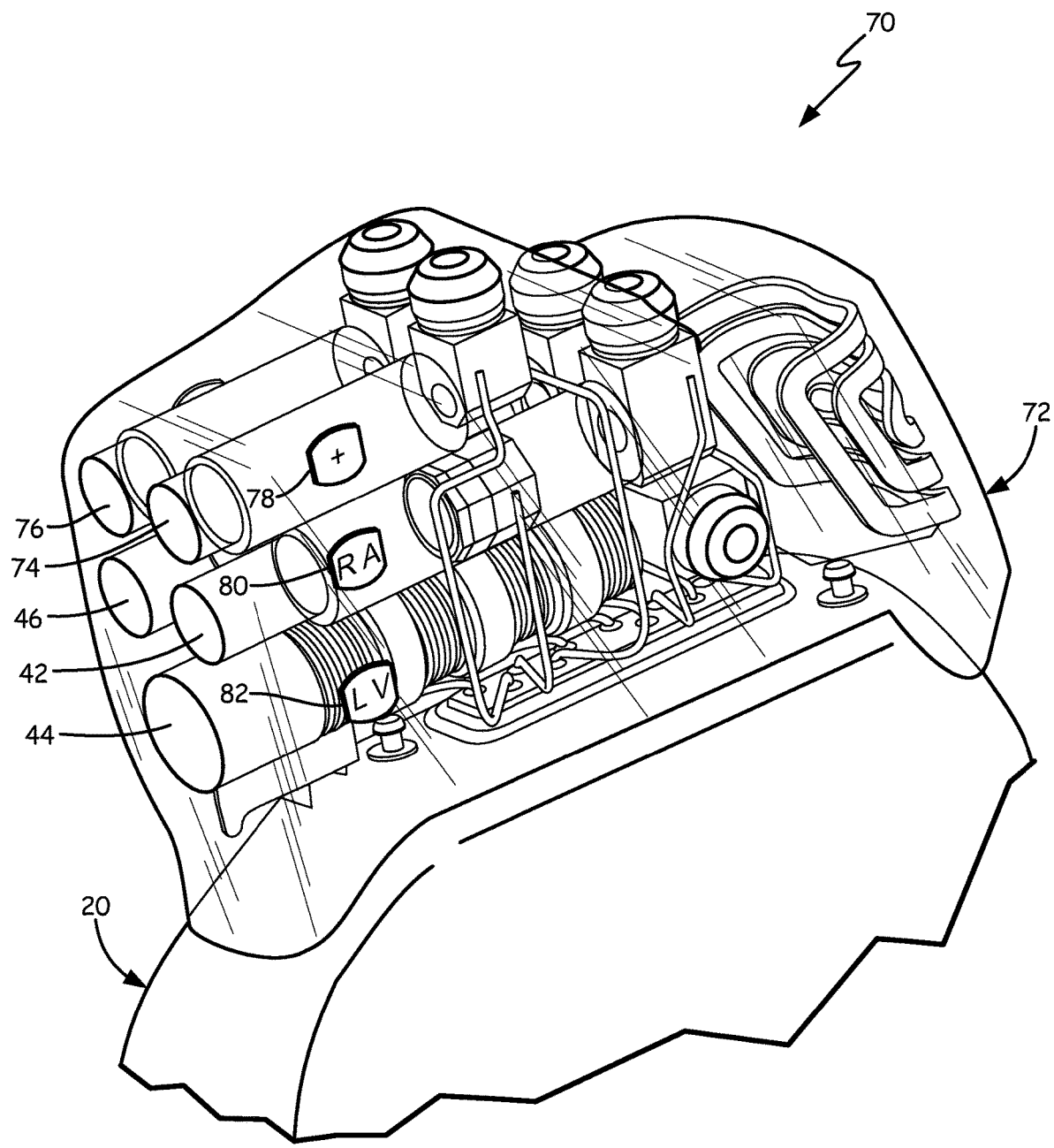
FIG. 4A is a perspective view of one side of an alternative embodiment of the pulse generator of FIG. 2.
Figure 4B:
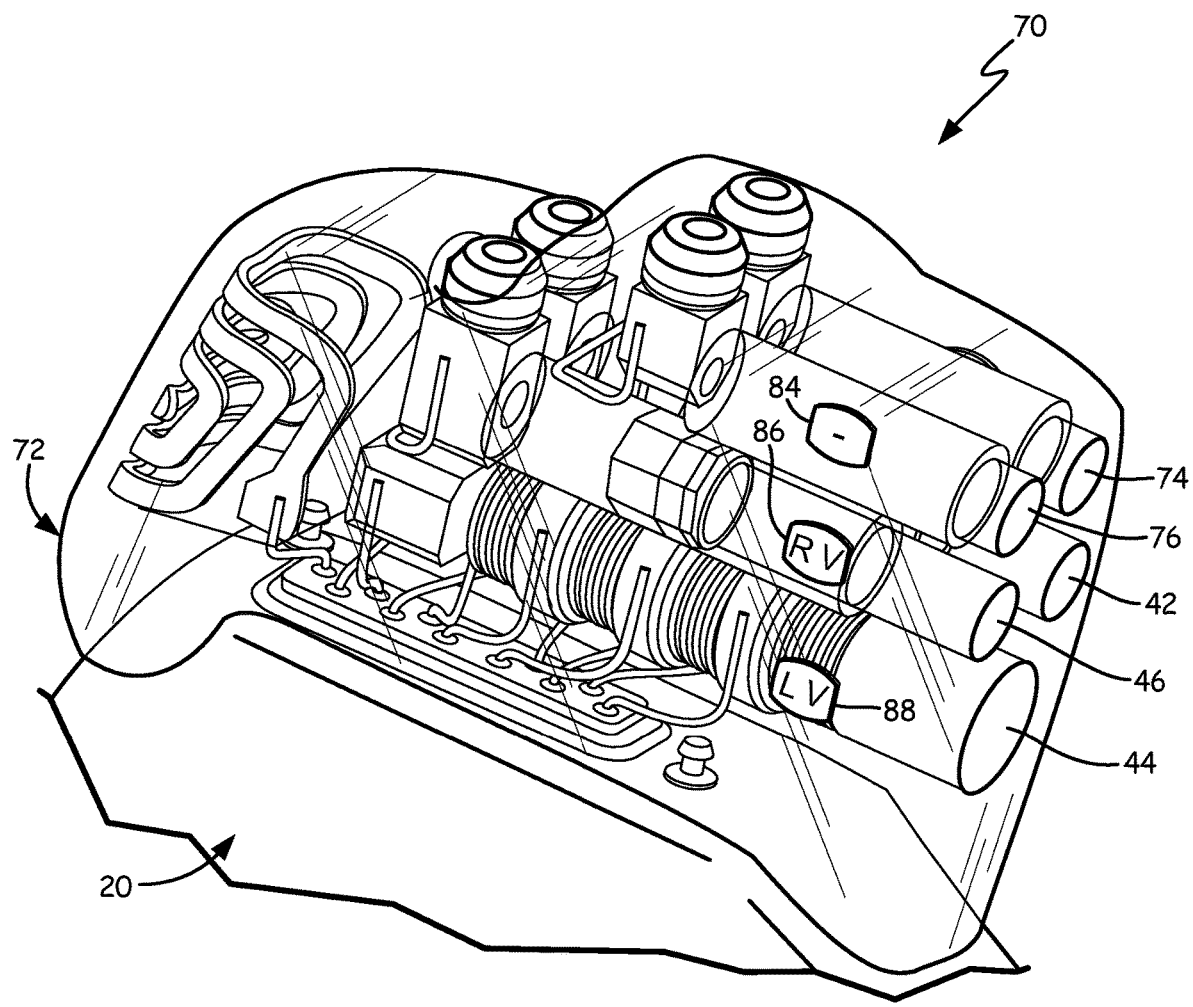
FIG. 4B is a perspective view of another side of the pulse generator of FIG. 4A.

FIGS. 4A and 4B are partial perspective views of opposite sides of a pulse generator 70, which is an alternative embodiment of the pulse generator 12. The pulse generator 70 is similar to the pulse generator 12 except the pulse generator 70 includes a header 72 with additional lead bore cavities 74 and 76, in addition to the lead bore cavities 42, 44, and 46.

FIG. 4A shows a label 78 proximate the lead bore cavity 74. The label 78 can be printed with a "+" shaped indicium and/or a blue pigment. A label 80 is proximate the lead bore cavity 42. The label 80 can be printed with indicia of "RA" and/or a white pigment. A label 82 is proximate the lead bore cavity 44. The label 82 can be printed with indicia of "LV" and/or a green pigment.

As shown in FIG. 4B, the header 72 further includes a label 84 proximate the lead bore cavity 76. The label 84 can be printed with a "−" shaped indicium and/or a red pigment. A label 86 is proximate the lead bore cavity 46. The label 86 can be printed with indicia of "RV" and/or a white pigment. A label 88 is proximate the lead bore cavity 44. The label 88 can be printed with indicia of "LV" and/or a green pigment. In the illustrated embodiment, the label 88 is identical to the label 82 (shown in FIG. 4A), as both of the labels 82 and 88 are printed proximate, are printed onto opposite sides of, and identify the same lead bore cavity 44.

In various embodiments, respective labels can be configured to include multiple sections, regions or features having different characteristics (e.g., different colors, brightness under fluoroscopy, etc.) so as to further enhance the visibility of desired indicia.

Figure 5:
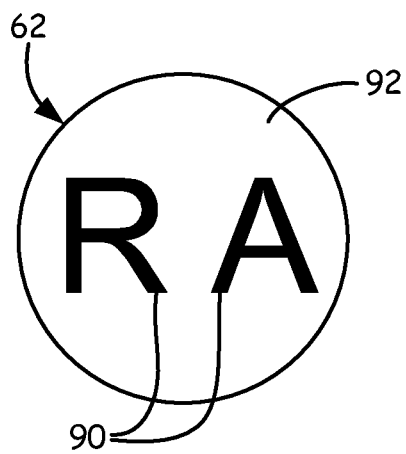
FIG. 5 is an enlarged view of a label used on a header of the pulse generator of FIG. 2.

FIG. 5 is an enlarged view of the label 62 according to an exemplary embodiment. In some embodiments, the label 62 can be printed so as to define first and second portions 90 and 92. The first portion 90 is shaped as the indicia "RA", and the second portion 92 is the portion surrounding the indicia "RA". In one embodiment, the first portion 90 can be black and the second portion 92 can be white. In other embodiments, the first and second portions 90 and 92 can have other colors so long as such colors have suitable contrast. In one embodiment, the label 62 can be printed by first printing a white circle-shaped background and then printing the first portion 90 on top of that background. In another embodiment, the label 62 can be printed by first printing a black circle-shaped background and then printing the second portion on top of that background. In other embodiments, the label 62 can be printed by printing the first and second portions separately onto a different background or onto no background at all.

In some embodiments, the label 62 can be printed with a radiopaque ink which has one or more radiopaque constituents. This can allow the indicia defined by the first portion 90 to be viewable via radiology imaging systems (such as x-ray systems). In one embodiment, the first portion 90 can be printed using radiopaque constituents while the second portion 92 is printed without radiopaque constituents. Thus, the indicia defined by the first portion 90 can appear lightly colored in a radiology imaging system. In another embodiment, the first portion 90 can be printed without radiopaque constituents while the second portion 92 is printed with radiopaque constituents. Thus, the indicia defined by the first portion 90 can appear darkly colored in a radiology imaging system, as having an absence of radiopaque constituents. One, more, or all of the labels 50, 52, 54, 62, 64, 66, 78, 80, 82, 84, 86, and 88 can be printed using radiopaque ink allowing radiology imaging systems to distinguish between different labels. Use of radiopaque ink can allow for labels to be identified and distinguished not only during the implantation of a pulse generator (such as pulse generators 12 and 70), but also after the pulse generator has been implanted into a patient's body.

Figure 6:
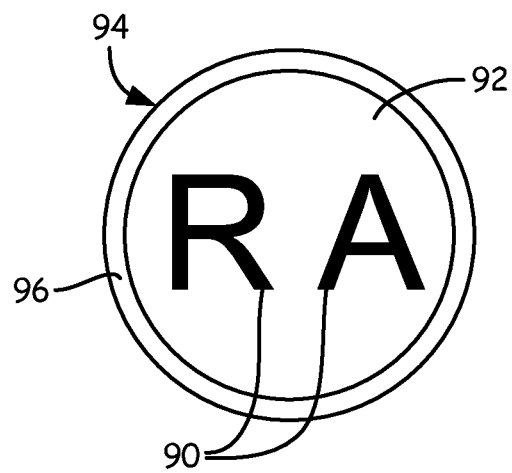
FIG. 6 is an enlarged view of an alternative embodiment of the label of FIG. 5.

FIG. 6 is an enlarged view of a label 94, which is similar to the label 62 except the label 94 is printed with a border 96. The border 96 can increase contrast and help improve visibility of the label 94. In embodiments where the second portion 92 has a light color, the border 96 can be black or a dark color. In embodiments where the second portion has a dark color, the border 96 can be white or a light color.

Figure 7:
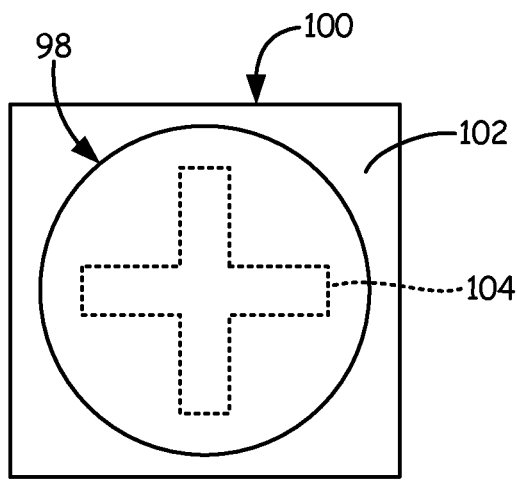
FIG. 7 is an enlarged view of another alternative embodiment of the label of FIG. 5, covered by a lens.

FIG. 7 is an enlarged view of a label 98 covered by a lens 100. The label 98 can include one or more colors and/or one or more indicia (such as the indicium 104). In one embodiment, the lens 100 includes a surface 102 that is convex so as to magnify the label 98 and any indicia thereon. Using the lens 100 for magnification can allow the label 98 to be printed relatively small while still being viewable.

In another embodiment, the lens 100 can be a lenticular lens with the surface 102 including an array of magnifying lenses suitable for magnifying different images from different angles. The label 98 can be printed with multiple images suitable for use with the lens 100 to produce different appearances when viewed from different angles. For example, in one embodiment, the label 98 can appear from a first angle as a colored label (showing for example red, white, green, or blue) without showing or without clearly showing indicia (such as the indicium 104). The label 98 can then appear from a second angle as a label having the indicium 104 (showing for example "RA", "RV", "LV", "+", or "−"). In one embodiment, the lens 100 can be operably positioned proximate one or more labels (such as the labels 50, 52, 54, 62, 64, 66, 78, 80, 82, 84, 86, and 88). In alternative embodiments, one or more labels can each have its own lenticular lens.

Therefore, as described above, pulse generators (such as the pulse generators 12 and 70) can include one or more labels having color, indicia, or both that can help identify and distinguish different lead bore cavities. This can assist physicians in readily and efficiently identifying the different lead bore cavities for connecting to corresponding leads. Printing labels onto a core and then overmolding over the core can allow for efficient encapsulation of the labels and can hermetically seal the labels from patient contact. Encapsulating the labels can allow for use of a number of pigments that do not appear in 21 C.F.R. 73 (Listing of Color Additives Exempt From Certification), 21 C.F.R. 74 (Listing of Color Additives Subject to Certification), and (21 C.F.R. 82 Listing of Certified Provisionally Listed Colors and Specifications), which can allow for selection of colors that improve contrast. Use of machine-readable indicia, ink having radiopaque constituents, magnifying and lenticular lenses, and/or specialized inks or brighteners can further improve a physician's ability to identify and distinguish different lead bore cavities both during and after implantation of the pulse generators.

In a variation of each of the above described embodiments, the header body may be molded or otherwise formed as described above but without one or more of the labels being embedded within the material of the header body. For each of the labels not embedded with the header body, a recess can be ground, drilled, or otherwise formed within the material of the header body. Each recess can be dimensioned to receive the label. For example, the depth, length, and width (or radius), of the recess can be larger than the thickness, length, and width (or radius) of the label such that the label fits entirely within the recess and no part of the label protrudes out of the recess (e.g., beyond the outer surface of the header body). The recess can then be filled in with material to partially or fully encapsulate the label within the recess. The material can fully cover the label within the recess. The label may be entirely sealed within the recess such that no part of the label is exposed on an exterior of the pulse generator and that no part of the label may come into contact with tissue or fluids of the patient. The recess may be filled in the same manner as any molding step referenced herein, including an over molding step. The recess may be filled with an adhesive material that is injected into the recess or poured into the recess. Suitable materials for filling the recess and encapsulating the label include epoxy, acrylic, polymer (silicone, urethane), and/or any other material referenced herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable pulse generator system comprising:
   a header connected to a device housing, the header including:
   a core assembly defining first and second lead bore cavities;
   a first label formed from a first ink having a first pigment printed onto and in contact with a surface of the core assembly proximate the first lead bore cavity, wherein the first label comprises a first color;
   a second label formed from a second ink having a second pigment, different from the first pigment, printed onto and in contact with the surface of the core assembly proximate the second lead bore cavity, wherein the second label comprises a second color different from the first color; and
   a first lens in contact with and covering a portion of at least one of the first label and the second label.

2. The implantable pulse generator system of claim 1, further including:
   a first lead having a first terminal pin and a first lead label of a hue that is substantially the same as that of the first color; and
   a second lead having a second terminal pin and a second lead label of a hue that is substantially the same as that of the second color.

3. The implantable pulse generator system of claim 2, further including:

a second lens positioned proximate to at least one of the first lead label and the second lead label.

4. The implantable pulse generator system of claim 3, wherein the at least one of the first label and the second label proximate to the first lens and the at least one of the first lead label and the second lead label proximate to the second lens include multiple images such that different appearances are produced when viewed through the first and second lens at different angles.

5. The implantable pulse generator system of claim 4, wherein the first and second lens are lenticular lens.

6. The implantable pulse generator system of claim 3, wherein the first label includes radiopaque ink patterned to define a first indicia and the second label includes radiopaque ink patterned to define a second indicia that is different from the first indicia, wherein the first lead label includes radiopaque ink patterned to define a third indicia and the second lead label includes radiopaque ink patterned to define a fourth indicia different from the third indicia, and wherein the first, second, third, and fourth indicia is viewable via radiology imaging systems.

7. The implantable pulse generator system of claim 3, wherein the first label includes radiopaque ink patterned to define a first indicia and the second label includes radiopaque ink patterned to define a second indicia that is different from the first indicia, wherein the first lead label includes radiopaque ink patterned to define a third indicia and the second lead label includes radiopaque ink patterned to define a fourth indicia different from the third indicia, and wherein the first, second, third, and fourth indicia is viewable in the visible light spectrum.

8. The implantable pulse generator system of claim 1, wherein the core assembly includes an engineered thermoplastic polyurethane.

9. The implantable pulse generator system of claim 1, wherein the first label includes a first machine-readable indicia, the second label includes a second machine-readable indicia different from the first machine-readable indicia, the first lead label includes a third machine-readable indicia, and the second lead label includes a fourth machine-readable indicia different from the third machine-readable indicia.

10. The implantable pulse generator system of claim 9, wherein the first machine-readable indicia corresponds to the third machine-readable indicia and the second machine-readable indicia corresponds to the fourth machine-readable indicia.

11. The implantable pulse generator system of claim 1, further includes:
an outer layer overmolded over the core assembly so as to encapsulate the first and second labels from an external environment and to allow access to the first and second lead bore cavities.

12. The implantable pulse generator system of claim 11, wherein the outer layer is transparent.

13. The implantable pulse generator system of claim 12, further including:
a device housing containing pulse generator circuitry.

14. An implantable pulse generator system comprising:
a header connected to a device housing, the header including:
a core assembly defining first and second lead bore cavities;
a first label formed from a first ink having a first pigment printed onto and in contact with a surface of the core assembly proximate the first lead bore cavity, wherein the first label comprises a first color; and
a second label formed from a second ink having a second pigment, different from the first pigment, printed onto and in contact with the surface of the core assembly proximate the second lead bore cavity, wherein the second label comprises a second color different from the first color;
a first lead having a first terminal pin and a first lead label of a hue that is substantially the same as that of the first color;
a second lead having a second terminal pin and a second lead label of a hue that is substantially the same as that of the second color; and
a first lens in contact with and covering a portion of at least one of the first lead label and the second lead label.

15. The implantable pulse generator system of claim 14, further including:
a second lens positioned proximate to at least one of the first label and the second label.

16. The implantable pulse generator system of claim 15, wherein the at least one of the first label and the second label proximate to the first lens and the at least one of the first lead label and the second lead label proximate to the second lens include multiple images such that different appearances are produced when viewed through the first and second lens at different angles.

17. The implantable pulse generator system of claim 15, wherein the first and second lens are lenticular lens.

18. The implantable pulse generator system of claim 14, further including:
a device housing containing pulse generator circuitry;
an outer layer overmolded over the core assembly so as to encapsulate the first and second labels from an external environment and to allow access to the first and second lead bore cavities.

19. A method of labeling a header of an implantable pulse generator, the method comprising:
printing a first label and a second label onto a surface of a core assembly, the first label proximate a first lead bore cavity and the second label proximate a second lead bore cavity;
printing a third label on a first lead configured to be received within the first lead bore cavity;
printing a fourth label on a second lead configured to be received within the second lead bore cavity;
positioning a first lens in contact with and covering a portion of at least one of the first label and the second label;
positioning a second lens in contact with and covering a portion of at least one of the third label and the fourth label.

20. The method of claim 19, further including:
patterning a first set of indicia onto the first label and a second set of indicia different from the first set of indicia onto the second label; and
patterning a third set of indicia onto the third label and a fourth set of indicia different from the third set of indicia onto the fourth label.

* * * * *